United States Patent
Jeong et al.

(10) Patent No.: US 9,833,290 B2
(45) Date of Patent: Dec. 5, 2017

(54) MINIMALLY INVASIVE SURGICAL INSTRUMENT

(76) Inventors: Chang Wook Jeong, Seoul (KR);
Hyung Tae Kim, Incheon (KR)

(*) Notice: Subject to any disclaimer, the term of this patent is extended or adjusted under 35 U.S.C. 154(b) by 844 days.

(21) Appl. No.: 13/979,550

(22) PCT Filed: Dec. 29, 2011

(86) PCT No.: PCT/KR2011/010345
§ 371 (c)(1),
(2), (4) Date: Sep. 26, 2013

(87) PCT Pub. No.: WO2012/096464
PCT Pub. Date: Jul. 19, 2012

(65) Prior Publication Data
US 2014/0194893 A1 Jul. 10, 2014

(30) Foreign Application Priority Data
Jan. 12, 2011 (KR) .................. 10-2011-0003192

(51) Int. Cl.
*A61B 19/00* (2006.01)
*A61B 17/29* (2006.01)
(Continued)

(52) U.S. Cl.
CPC ........ *A61B 19/22* (2013.01); *A61B 17/00234* (2013.01); *A61B 17/29* (2013.01);
(Continued)

(58) Field of Classification Search
CPC ... A61B 17/00; A61B 17/00234; A61B 17/29; A61B 2017/2901; A61B 2017/00292;
(Continued)

(56) References Cited

U.S. PATENT DOCUMENTS 5,792,165 A * 8/1998 Klieman ............... A61B 17/29
606/170
6,817,974 B2 * 11/2004 Cooper ............ A61B 17/00234
600/142
(Continued)

FOREIGN PATENT DOCUMENTS

EP            1886630 A2    2/2008
KR   10-2005-0075451 A     7/2005
(Continued)

OTHER PUBLICATIONS

International Search Report PCT/KR2011/010345 dated Jun. 22, 2012.

*Primary Examiner* — Ahmed Farah
(74) *Attorney, Agent, or Firm* — Dinsmore & Shohl LLP (57) ABSTRACT

The present invention relates to a convenient, minimally invasive surgical instrument, and more particularly to a minimally invasive surgical instrument to allow a user to operate an end effector by manipulating a handling unit or the like to perform a minimally invasive surgery in a delicate and convenient manner. According to one aspect of the invention, there is provided a minimally invasive surgical instrument comprising: a shaft; an end effector being connected to one end of the shaft via a joint unit; a rotation manipulation unit being connected to the other end of the shaft, the rotation manipulation unit comprising a gyro link including a gyro wheel; and a plurality of wires being connected between the joint unit and the gyro wheel, wherein the end effector carries out joint motion by the joint unit according to the action of at least some of the plurality of wires caused by a manipulation of the gyro wheel.

22 Claims, 9 Drawing Sheets

(51) Int. Cl.
*A61B 34/00* (2016.01)
*A61B 17/062* (2006.01)
*A61B 17/00* (2006.01)
*A61B 17/068* (2006.01)

(52) U.S. Cl.
CPC .......... *A61B 34/70* (2016.02); *A61B 17/062* (2013.01); *A61B 17/068* (2013.01); *A61B 2017/00314* (2013.01); *A61B 2017/00323* (2013.01); *A61B 2017/291* (2013.01); *A61B 2017/2929* (2013.01)

(58) Field of Classification Search
CPC .... A61B 2017/003; A61B 2017/00305; A61B 2017/00314; A61B 2017/00318; A61B 2017/00232; A61B 2017/00327; A61B 2017/00363; A61B 19/20; A61B 19/52; A61B 19/201; A61B 19/203; A61B 19/5244

USPC ..................................................... 606/1, 130
See application file for complete search history.

(56) References Cited

U.S. PATENT DOCUMENTS

| 2002/0040217 | A1 | 4/2002 | Jinno |
| 2007/0282371 | A1* | 12/2007 | Lee ...................... A61B 17/062 606/205 |
| 2010/0087818 | A1* | 4/2010 | Cunningham ......... A61B 17/29 606/53 |
| 2011/0125166 | A1 | 5/2011 | Cooper et al. |
| 2012/0253324 | A1* | 10/2012 | Lee .................... A61B 1/00071 606/1 |

FOREIGN PATENT DOCUMENTS

| KR | 10-2009-0051049 A | 5/2009 |
| WO | WO 2008-020964 A2 | 2/2008 |

* cited by examiner

MINIMALLY INVASIVE SURGICAL INSTRUMENT

FIELD OF THE INVENTION

The present invention relates to a convenient, minimally invasive surgical instrument, and more particularly to a minimally invasive surgical instrument to allow a user to operate an end effector by manipulating a handling unit or the like to perform a minimally invasive surgery in a delicate and convenient manner.

BACKGROUND

Minimally invasive surgery is a surgical approach that involves the use of instruments inserted through several tiny incision openings to perform a surgery causing minimal tissue trauma in human or animal bodies.

The minimally invasive surgery relatively reduces changes in metabolism of a patient in the period of post-surgical care, so it facilitates rapid recovery of the patient. Therefore, the minimally invasive surgery shortens the length of hospitalization of the patient after the surgery and allows the patient to return to normal physical activities in a short period of time. In addition, the minimally invasive surgery causes less pain and leaves fewer scars on the patient's body after the surgery.

One of the general forms of the minimally invasive surgery is endoscopy. Among the others, a laparoscopy that involves minimally invasive inspection and operation inside abdominal cavity is known as the most general form of endoscopy. To operate a standard laparoscopic surgery, the abdomen of the patient is insufflated with gas and at least one small incision is formed to provide an entrance for laparoscopic surgical instruments, through which a trocar is inserted. When performing the surgery, it is general that a user puts the laparoscopic surgical instruments into a surgical site or the like through the trocar, and manipulates the instruments from the outside of abdominal cavity. In general, the laparoscopic surgical instruments include a laparoscope (for observation of a surgical site) and other working tools. Herein, the working tools are similar to the conventional tools used for small incision surgery, except that the end effector or working end of each tool is separated from its handle or the like by a shaft. For instance, the working tools may include a clamp, a grasper, scissors, a stapler, a needle holder, and so forth. Meanwhile, the user monitors the procedure of the surgery through a monitor that displays the images of the surgical site which are taken by the laparoscope. The endoscopic approaches similar to the above are broadly used in retroperitoneoscopy, pelviscopy, arthroscopy, cisternoscopy, sinuscopy, hysteroscopy, nephroscopy, cystoscopy, urethroscopy, pyeloscopy, and so on.

The inventor(s) has developed various minimally invasive surgical instruments useful for the above-mentioned minimally invasive surgeries and has already disclosed the features of the structures and effects of the same in Korean Patent Application Nos. 2008-51248, 2008-61894, 2008-79126 and 2008-90560, the contents of which are incorporated herein by reference in its entirety. Additionally, the inventor(s) will provide a minimally invasive surgical instrument with improved functionality, which is more advantageous for users and patients.

SUMMARY OF THE INVENTION

One object of the present invention is to provide a minimally invasive surgical instrument wherein its joint motion may be carried out smoothly and delicately.

Another object of this invention is to provide a minimally invasive surgical instrument wherein the joint motion state of its end effector may be easily fixed.

Yet another object of this invention is to provide a minimally invasive surgical instrument wherein the rolling of its end effector may be easily carried out.

Still another object of this invention is to provide a minimally invasive surgical instrument wherein the rolling of its end effector may be carried out while the joint motion state of the end effector is fixed and maintained.

According to one aspect of the invention to achieve the objects as described above, there is provided a minimally invasive surgical instrument, comprising: a shaft; an end effector being connected to one end of the shaft via a joint unit; a rotation manipulation unit being connected to the other end of the shaft, the rotation manipulation unit comprising a gyro link including a gyro wheel; and a plurality of wires being connected between the joint unit and the gyro wheel, wherein the end effector carries out joint motion by the joint unit according to the action of at least some of the plurality of wires caused by a manipulation of the gyro wheel.

In addition, there may be provided other ways to implement this invention.

According to the invention, there is provided a minimally invasive surgical instrument wherein its joint motion may be carried out smoothly and delicately.

According to the invention, there is provided a minimally invasive surgical instrument wherein the joint motion state of its end effector may be easily fixed.

According to the invention, there is provided a minimally invasive surgical instrument wherein the rolling of its end effector may be easily carried out.

According to the invention, there is provided a minimally invasive surgical instrument wherein the rolling of its end effector may be carried out while the joint motion state of the end effector is fixed and maintained.

DETAILED DESCRIPTION OF THE PREFERRED EMBODIMENTS

In the following detailed description of the invention, references are made to the accompanying drawings that show, by way of illustration, specific embodiments in which the invention may be practiced. These embodiments are described in sufficient detail to enable those skilled in the art to practice the invention. It is to be understood that the various embodiments of the invention, although different from each other, are not necessarily mutually exclusive. For example, specific shapes, structures, or characteristics described herein may be implemented as modified from one embodiment to another embodiment without departing from the spirit and the scope of the invention. Furthermore, it shall be understood that the locations or arrangements of individual elements within each embodiment may be also modified without departing from the spirit and the scope of the invention. Therefore, the following detailed description is not to be taken in a limiting sense, and the scope of the invention is to be taken as encompassing the scope of the appended claims and all equivalents thereof. In the drawings, like reference numerals refer to the same or similar elements throughout the several views.

Hereinafter, preferred embodiments of the present invention will be described in detail with reference to the accompanying drawings to enable those skilled in the art to easily implement the invention.

Figure 1:
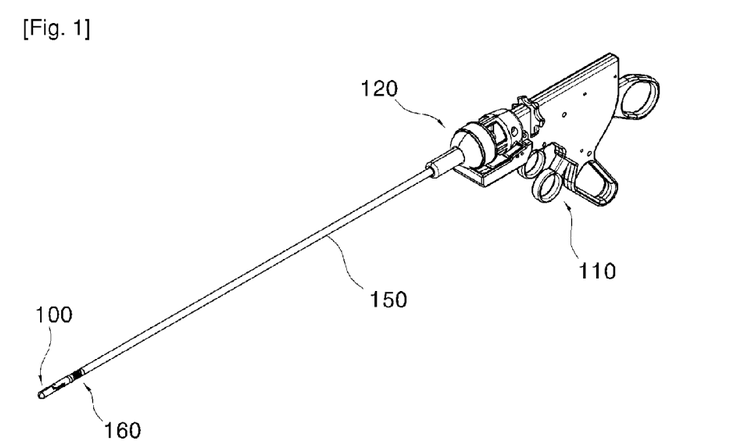
FIG. 1 is a perspective view showing the overall appearance of a minimally invasive surgical instrument according to one embodiment of the invention.
Figure 2:
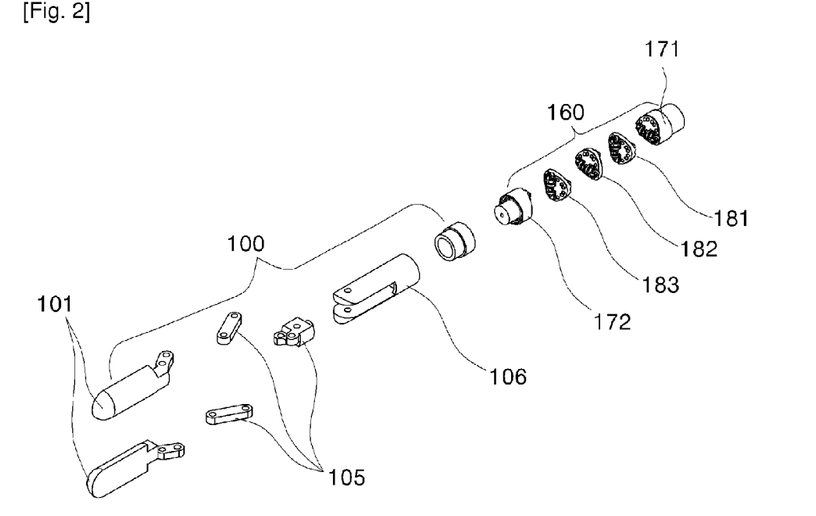
FIG. 2 is an exploded view of some elements shown in FIG. 1.

FIG. 1 is a perspective view showing the overall appearance of a minimally invasive surgical instrument according to one embodiment of the invention. Further, FIG. 2 is an exploded view of some elements shown in FIG. 1.

First, reference will be made to FIG. 1. The minimally invasive surgical instrument according to one embodiment of the invention may comprise an end effector 100 to perform surgery by using surgical instruments (not shown) or functioning itself as a surgical instrument; a handling unit 110 to control the operation of the end effector 110 according to the user's manipulation; a shaft 150 to connect the end effector 100 and the handling unit 110, wherein the end effector 100 is disposed at one end of the shaft 150 and the handling unit 110 is disposed at the other end of the shaft 150; a rotation manipulation unit 120 to connect the shaft 150 and the handling unit 110 to cause joint motion and perform a fixing function; and a joint unit 160 to connect the end effector 100 and the shaft 150 to carry out joint motion.

Next, reference will be made to FIG. 2. FIG. 2 shows main elements of the end effector 100 and the joint unit 160 according to one embodiment of the invention.

The end effector 100 may comprise pincers 101 (also referred to as "holder") to operate to hold objects such as surgical instruments; an X-shaped bellows link 105 being connected to one end of the pincers 101 to operate the pincers 101 to carry out expansion and contraction motion; and a support tube 106 being connected to the joint unit 160 to support and operate the bellows link 105. The support tube 106 may comprise a spring (not shown) to operate the bellows link 105, as necessary.

Meanwhile, the joint unit 160 may comprise a first connecting unit 171 and a second connecting unit 172 for connection to the shaft 150 and the end effector 100, as well as a first joint link 181, a second joint link 182 and a third joint link 183 being sequentially disposed therebetween. This will be discussed below in more detail.

Figure 3:
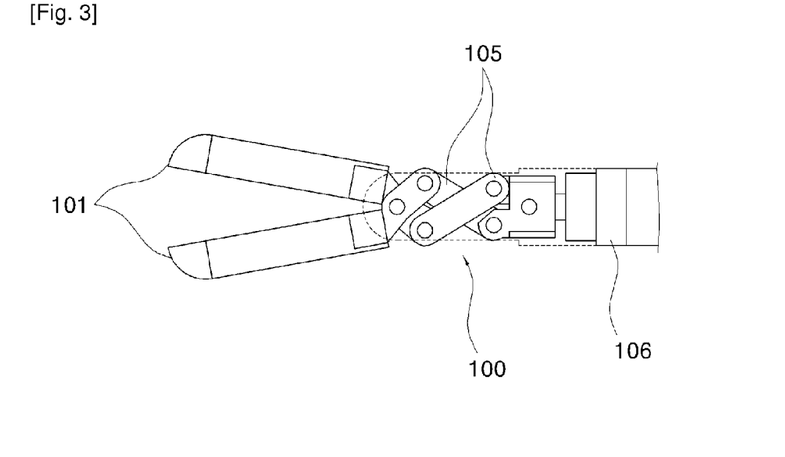
FIG. 3 is a lateral view of an end effector 100 according to one embodiment of the invention.

FIG. 3 is a lateral view of the end effector 100 according to one embodiment of the invention, which is shown partially transparently. (That is, there is shown transparently in the figure the interior of a housing to enclose the bellows link 105 and the support tube 106 so that the minimally invasive surgical instrument of the present invention may be used inside the body. It should be understood that even though not explicitly indicated, other elements may also be enclosed with such a housing, as necessary.) When opening/closing wires (not shown), which may be disposed between the end effector 100 and the handling unit 110, apply force to the bellows link 105 to expand it according to the user's manipulation of the handling unit 110, the bellows link 105 may expand from the default state as shown in FIG. 3 to close the pincers 101. (That is, the pincers 101 may pick up a surgical instrument or the like.) However, when such force is not applied to the bellows link 105, it contracts to open the pincers 101 by virtue of the restitution force of the spring as described above. (That is, the pincers 101 holding a surgical instrument or the like may release it.) Of course, the pincers 101 may be configured to close by default and otherwise open, as desired by those skilled in the art.

Figure 4:
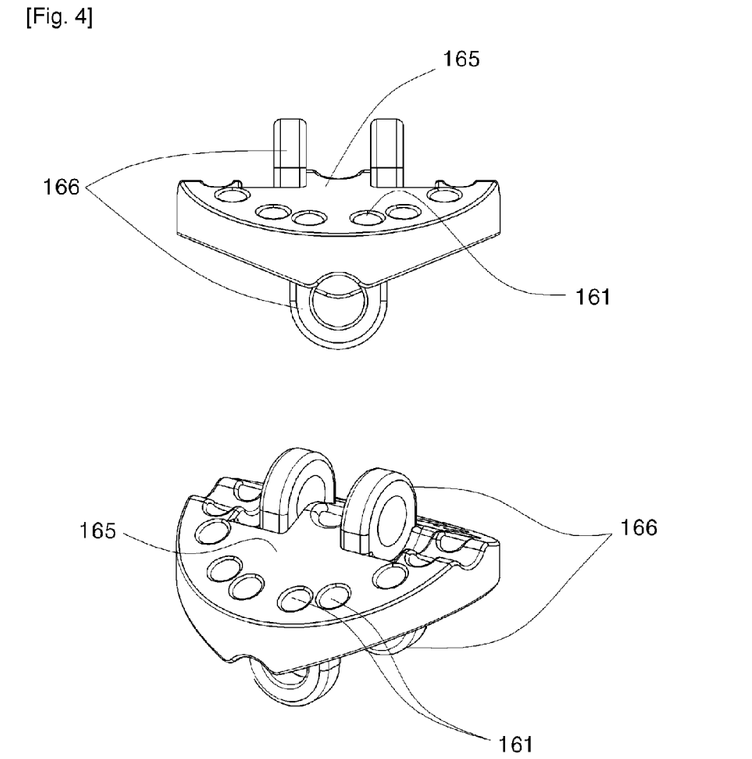
FIG. 4 is lateral and perspective views of a joint link according to one embodiment of the invention.
Figure 5:
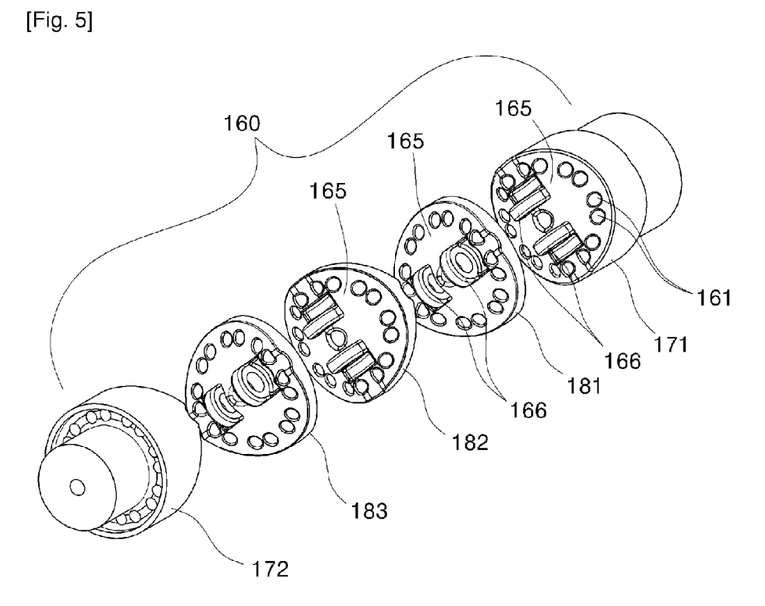
FIG. 5 is an exploded view of a joint unit 160 according to one embodiment of the invention.
Figure 6:
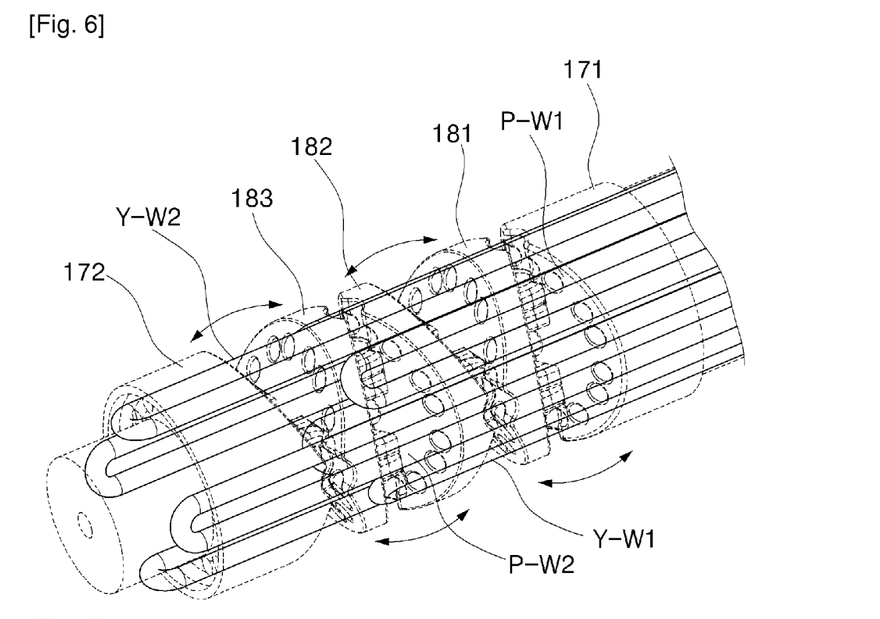
FIG. 6 shows a plurality of wires P-W1, Y-W1, P-W2 and Y-W2 arranged in the joint unit 160 shown in FIG. 5.

FIG. 4 is lateral and perspective views of the joint link according to one embodiment of the invention. FIG. 5 is an exploded view of the joint unit 160 according to one embodiment of the invention. Further, FIG. 6 shows a plurality of wires P-W1, Y-W1, P-W2 and Y-W2 arranged in the joint unit 160 shown in FIG. 5.

As described above and shown in FIGS. 4-6, the joint unit 160 may comprise a first connecting unit 171 and a second connecting unit 172 as well as a first joint link 181, a second joint link 182 and a third joint link 183. The joint link may comprise a plurality of via holes 161 to provide penetration passages for the wires P-W1, Y-W1, P-W2 or Y-W2 (the via holes may be paired with each other); a slope 165 to facilitate joint motion of the joint unit 160; and a rotating link 166 to provide rotatable connections between the joint links or between the connecting units and the joint links (the pivot for the rotating link 166 is not shown for convenience).

As shown in FIG. 4, two pairs of rotating links 166 belonging to a joint link may be disposed at both sides of the joint link, respectively. In this case, one pair of rotating links 166 may be oriented substantially perpendicular to the other pair of rotating links 166. Due to this configuration, the joint unit 160 may comprise joints for pitch direction operation of the end effector 100 (referred to as 'P') and joints for its yaw direction operation (referred to as 'Y') in the order of P-Y-P-Y (or Y-P-Y-P). In order to facilitate joint motion, a joint link may have a groove around its pair of rotating links 166, which is intended for a pair of rotating links 166 of another joint link (or connecting unit) engaged therewith.

Although the specific configuration of the joint links may be modified without limitation as desired by those skilled in the art, a plurality of via holes 161 may preferably be disposed close to the circumference of a joint link so that the torque applied to the joint link by the wires P-W1, Y-W1, P-W2 or Y-W2 passing through the via holes 161 (to be described below) may be as large as possible. In this case, the above-described rotating link 166 may be disposed close to the center of the joint link to suffer less interference from the wires P-W1, Y-W1, P-W2 or Y-W2.

Referring to FIG. 6 in conjunction with FIG. 5, it may be seen that each of a plurality of wires P-W1, Y-W1, P-W2 and Y-W2 for joint motion in the joint unit 160 may extend from the shaft 150 through the via holes 161 of the first connecting unit 171 to the first joint link 181, the second joint link 182, the third joint link 183, or the second connecting unit 172. It is apparent that the wires P-W1, Y-W1, P-W2 or Y-W2 may hang in the first joint link 181, the second joint link 182, the third joint link 183, or the second connecting unit 172 through the corresponding via holes. More wires of the same types as the plurality of wires P-W1, Y-W1, P-W2 and Y-W2 may also hang, all of which are not shown in FIG. 6.

Figure 7:
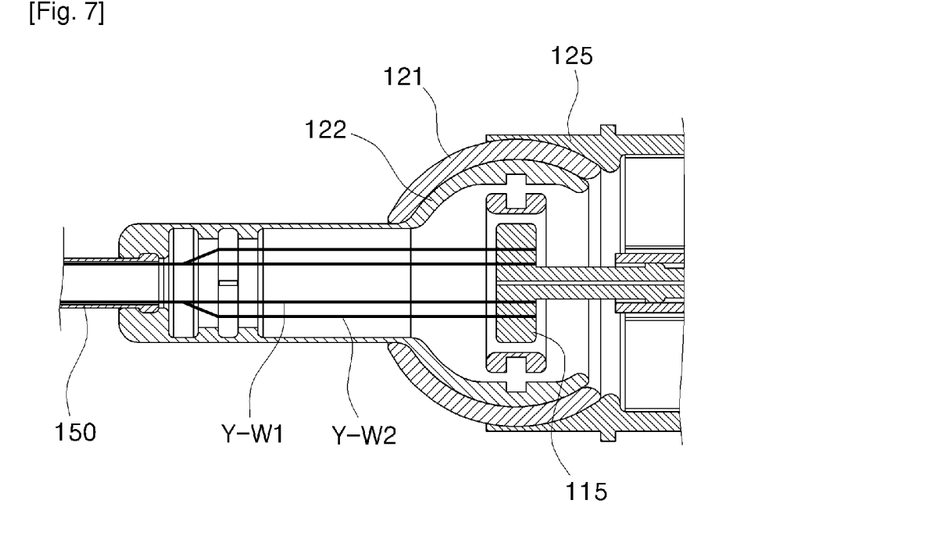
FIGS. 7 and 8 show the interior of a rotation manipulation unit 120 according to one embodiment of the invention.
Figure 8:
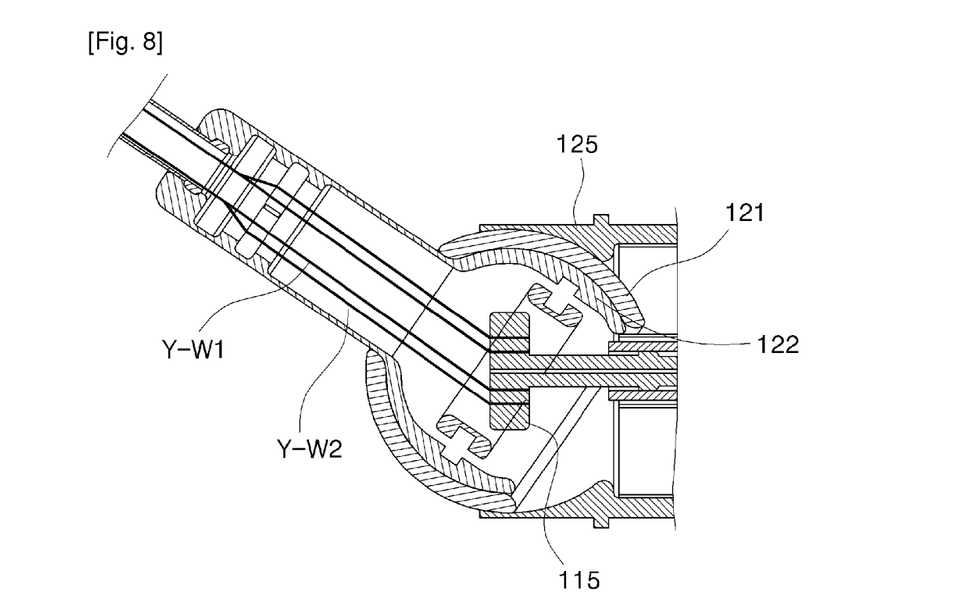
Figure 9:
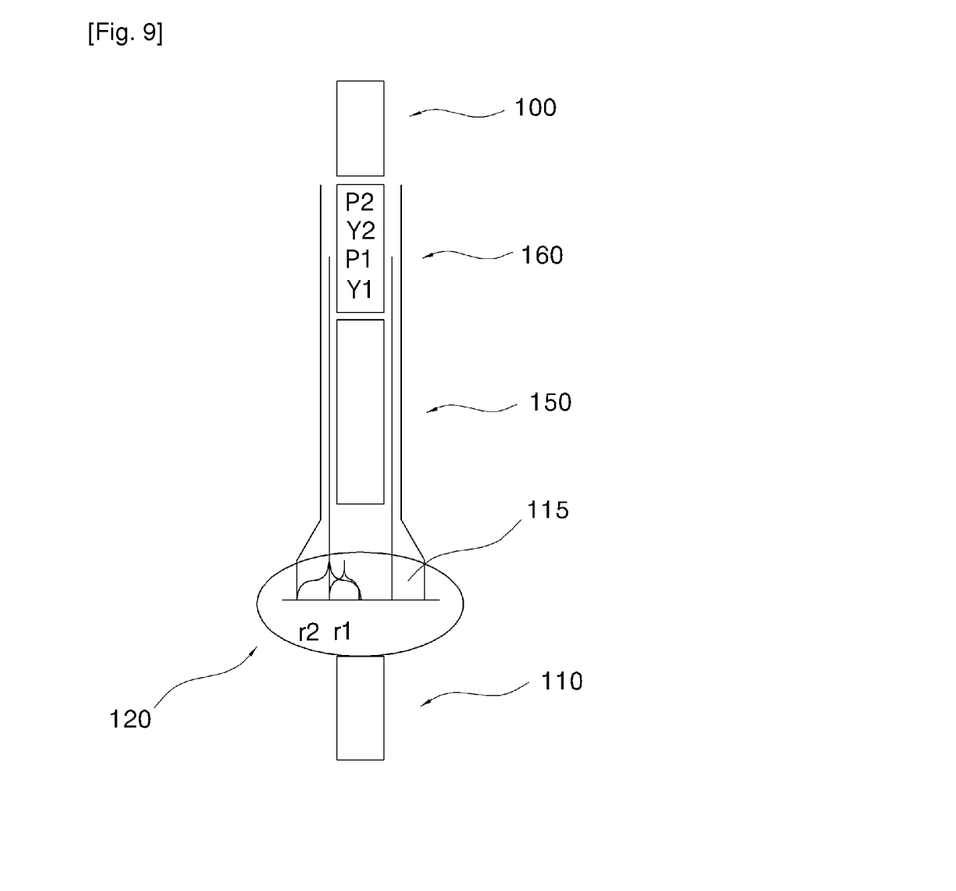
FIG. 9 shows how joint motion is carried out in the joint unit 160 by a gyro link 115 of the rotation manipulation unit 120 according to one embodiment of the invention.

FIGS. 7 and 8 show the interior of the rotation manipulation unit 120 according to one embodiment of the invention. Further, FIG. 9 shows how joint motion is carried out in the joint unit 160 by a gyro link 115 of the rotation manipulation unit 120 according to one embodiment of the invention.

First, the rotation angle of a yaw joint (i.e., a joint for yaw direction operation of the end effector 100, being formed between the first joint link 181 and the second joint link 182) will be referred to as YA1, where the joint motion of the yaw joint is carried out by the wire Y-W1. Further, the rotation angle of another yaw joint (i.e., a joint for yaw direction operation of the end effector 100, being formed between the third joint link 183 and the second connecting unit 172) will be referred to as YA2, where the joint motion of the yaw joint is carried out by the wire Y-W2.

As shown in FIG. 6-8, the wire Y-W1 extending to the second joint link 182 may connect to the inner one of the via holes of the gyro link 115 to be described below. Further, the wire Y-W2 extending to the second connecting unit 172 may connect to the outer one of the via holes of the gyro link 115. In this case, the distance between the inner via hole and the center of the gyro link 115 may be denoted as r1, and the distance between the outer via hole and the center of the gyro link 115 may be denoted as r2, as shown in FIG. 9.

According to the above-described configuration, if the user manipulates the handling unit 110 in the yaw direction by some angle (that is, the gyro wheel of the gyro link 115 operates in the yaw direction by some angle), thereby operating the end effector 100 in the yaw direction by the angle, then the relationship between the above-described variables may be approximately established as YA1: YA2=r1:(r2-r1). (In case of the pitch direction operation, the relationship may also be established as PA1:PA2=r1:(r2-r1).) Therefore, in implementing the minimally invasive surgical instrument according to the present invention, those skilled in the art may adjust the ratio of r1:r2 as necessary, thereby determining the distribution of the rotation angles in the joint unit 160 when the end effector 100 operates in the yaw or pitch direction. Preferably, those skilled in the art may determine the ratio of r1:r2=1:2 such that the ratio of YA1:YA2 and PA1:PA2 is about 1:1. Meanwhile, it should be noted that even when the ratio of r1:r2 changes variably, the value of YA1+Ya2 or PA1+PA2, i.e., the angle by which the end effector 100 eventually operates in the yaw or pitch direction, may be substantially constant if the handling unit 110 has been manipulated by a constant angle.

Figure 10:
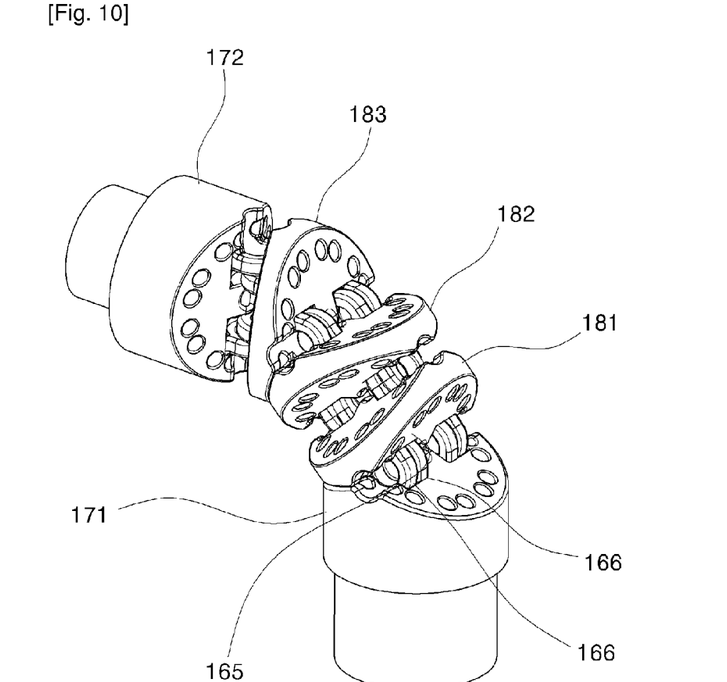
FIG. 10 shows the joint unit 160 in which the joint motion has been carried out according to one embodiment of the invention.

FIG. 10 shows the joint unit 160 in which the joint motion has been carried out according to one embodiment of the invention. As shown in FIG. 10, the first connecting unit 171 possibly abutting the first joint link 181 and the second connecting unit 172 possibly abutting the third joint link 183 may be respectively connected to the first joint link 181 and the third joint link 183 by the rotating links 166, where a slope similar to the slope 165 of the joint link may be included in the corresponding side. The rotation angle of the joint unit 160 in the pitch and yaw directions may preferably range from +90 degrees to −90 degrees. In this case, the inclination angle between the connecting unit and the slope 165 of the joint link may be uniform at 22.5 degrees.

Figure 11:
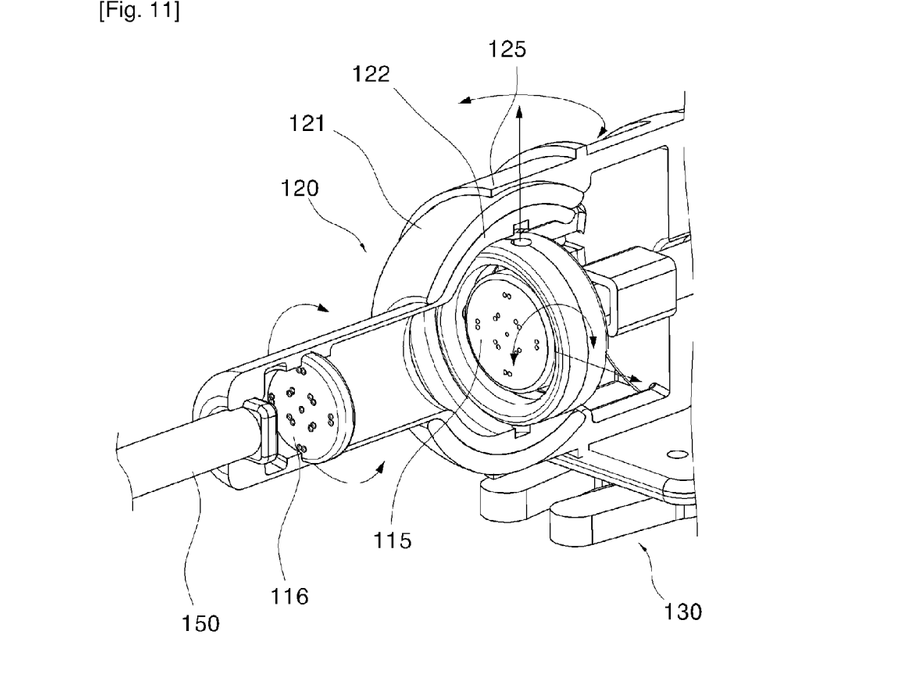
FIG. 11 is a detailed diagram of the rotation manipulation unit 120 according to one embodiment of the invention.

FIG. 11 is a detailed diagram of the rotation manipulation unit 120 according to one embodiment of the invention.

As shown in FIG. 11, the rotation manipulation unit 120 may comprise a gyro link 115, which may carry out gyroscopic motion while being connected to a plurality of wires P-W1, Y-W1, P-W2 and Y-W2 as described above, as well as rotating drums 121 and 122 or the like.

First, the plurality of wires P-W1, Y-W1, P-W2 and Y-W2 may hang in the gyro wheel of the gyro link 115. (To this end, the gyro wheel of the gyro link 115 may also have a plurality of (inner and outer) via holes.) Accordingly, in using the minimally invasive surgical instrument according to the present invention, the user may fix the shaft 150 at the position of a trocar or the like and then grab the handling unit 110 to operate the handing unit 110 in the pitch or yaw direction against the shaft 150 (i.e., to operate the gyro wheel of the gyro link 115 in the pitch or yaw direction against the shaft 150) so that the wires P-W1, Y-W1, P-W2 or Y-W2 may be generally pushed or pulled to allow joint motion for the end effector 100 to be carried out in the joint unit 160. Meanwhile, a penetration link 116 may be further disposed in the rotation manipulation unit 120 to provide intermediate penetration passages for the plurality of wires P-W1, Y-W1, P-W2 and Y-W2.

Next, the other elements of the rotation manipulation unit 120 will be discussed below. The rotation manipulation unit 120 may primarily comprise an external rotating drum 121 and an internal rotating drum 122, and the internal rotating drum 122 contains the gyro link 115 and the penetration link 116 therein and may operate only in the roll direction against the external rotating drum 121. Usually, the handling unit 110 may operate in the pitch or yaw direction against the external rotating drum 121 and the internal rotating drum 122 according to the user's manipulation of the handling unit 110 (that is, the gyro wheel of the gyro link 115 may operate in the pitch or yaw direction against the external rotating drum 121 and the internal rotating drum 122), which may lead to joint motion in the joint unit 160. However, when the user activates a rotating drum fixing means 130, a rotating drum fixing member 125 (preferably an annular member comprised of multiple segments) surrounding the external rotating drum 121 may be fastened to fix the handling unit 110 to the external rotating drum 121 and thus prevent any (subsequent) joint motion in the joint unit 160.

Figure 12:
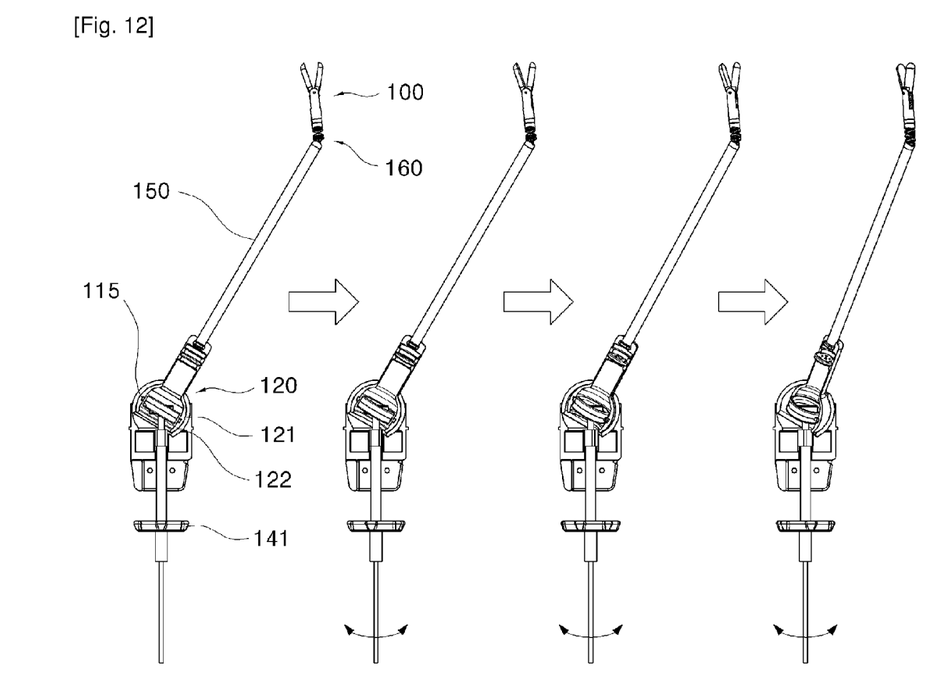
FIG. 12 shows a sequence of the rolling operation of the end effector 100 according to one embodiment of the invention.

Further reference will be made to FIG. 12. FIG. 12 shows a sequence of the rolling operation of the end effector 100 according to one embodiment of the invention.

As shown in FIG. 12 and described below, the handling unit 110 may be provided with a roll sprocket 141. When the user rotates the roll sprocket 141, the gyro wheel of the gyro link 155 may operate together in the roll direction. This leads to the roll direction operations of the internal rotating drum 122 (directly connected with the gyro link 115) and the shaft 150 fixed thereto, which eventually results in the roll direction operation of the end effector 100.

In the above case, the handling unit 110 and the external rotating drum 121 may be fixed to each other as described above, and under such conditions the joint motion in the joint unit 160 of the end effector 100 may be restricted while the roll direction operation of the plurality of wires P-W1, Y-W1, P-W2 and Y-W2 hung in the gyro link 115 may be unrestricted. Therefore, the roll direction operation of the wires P-W1, Y-W1, P-W2 and Y-W2 causes their changed tension to act in the joint unit 160 (as well as to act in consonance with the roll direction operation of the shaft 150) such that the end effector 100 may operate in the roll direction as shown in FIG. 12 while maintaining the joint motion state in the joint unit 160.

Figure 13:
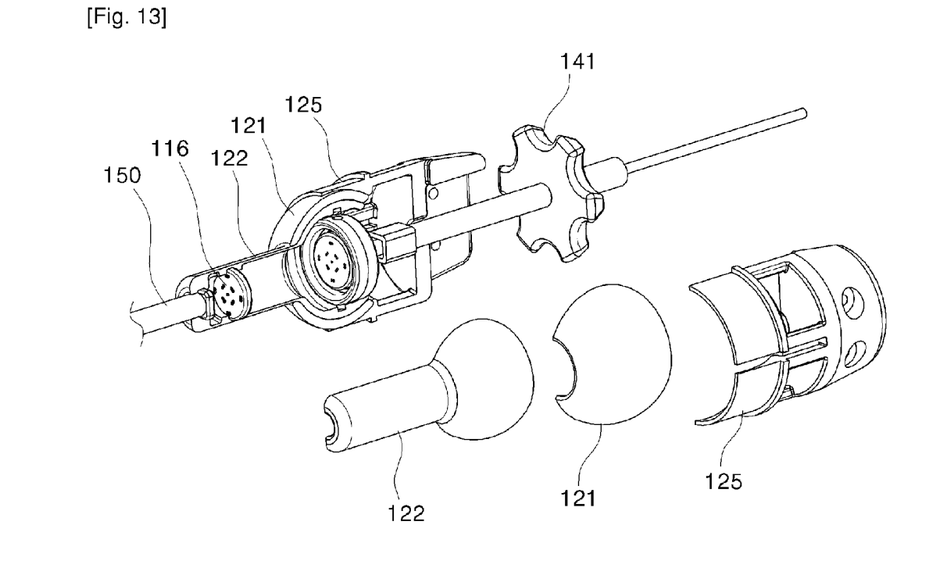
FIG. 13 is an exploded view of the rotation manipulation unit 120 according to one embodiment of the invention.
Figure 14:
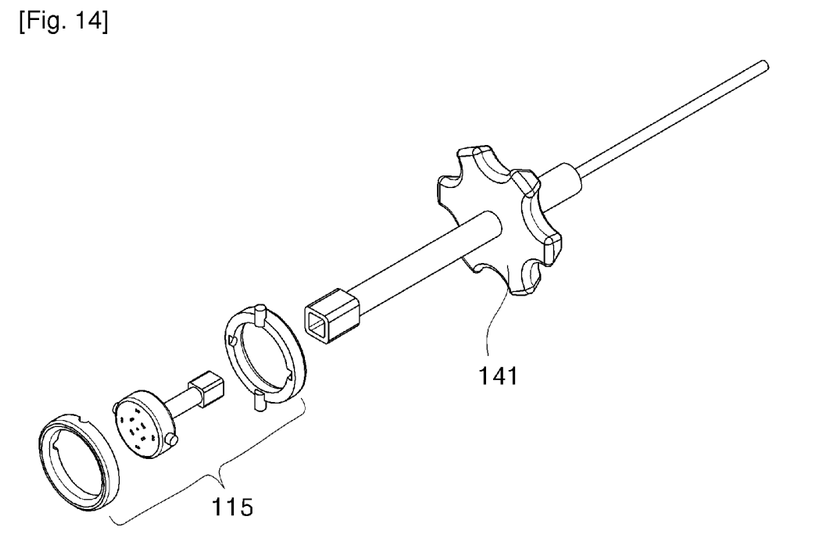
FIG. 14 is an exploded view of the gyro link 115 according to one embodiment of the invention.
Figure 15:
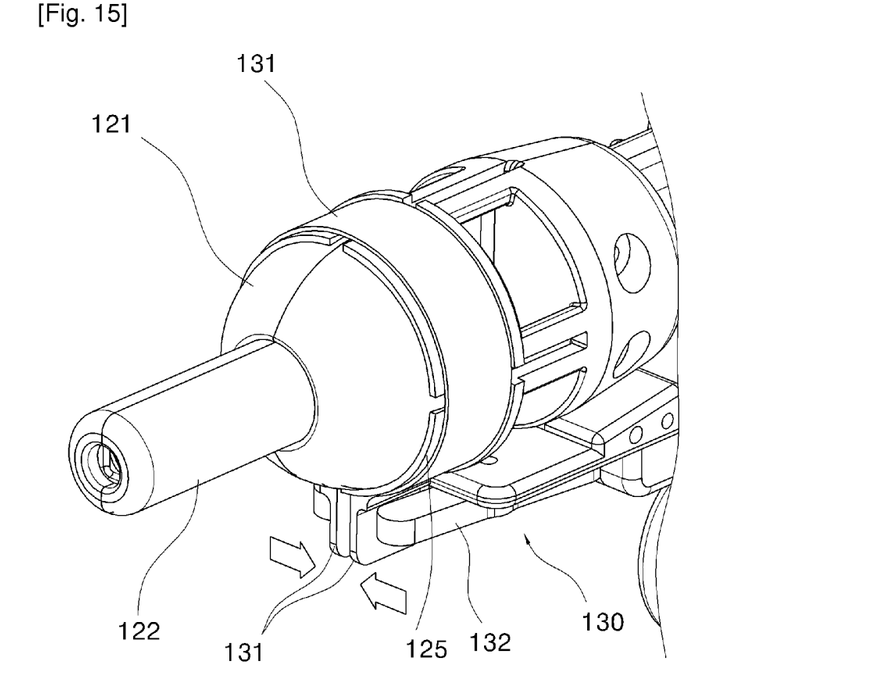
FIG. 15 shows a specific example of a configuration to fix a handling unit 110 to an external rotating drum 121 according to one embodiment of the invention.

With regard to the arrangements and connections of the above-described elements, further reference will be made to FIGS. 13-15. FIG. 13 is an exploded view of the rotation manipulation unit 120 according to one embodiment of the invention. FIG. 14 is an exploded view of the gyro link 115 according to one embodiment of the invention. Further, FIG. 15 shows a specific example of a configuration to fix the handling unit 110 to the external rotating drum 121 according to one embodiment of the invention.

As shown in FIG. 13, one end of the internal rotating drum 122 is engaged with the angular end of the shaft 150. Thus, when the internal rotating drum 122 rotates in the roll direction, the shaft 150 may operate together in the roll direction. A part of the internal rotating drum 122 may be contained in the external rotating drum 121, as illustrated. Accordingly, the internal rotating drum 122 may only carry out the roll direction operation independently from the external rotating drum 121. As illustrated, the rotating drum fixing member 125 connected to the handling unit 110 may be an annular member comprised of multiple segments and thus may be easily fastened. As the rotating drum fixing member 125 is fastened, the handling unit 110 may be fixed to the external rotating drum 121. Referring further to FIG. 15, the internal diameter of a rotating drum fixing ring 131 surrounding the rotating drum fixing member 125 may be reduced by a rotating drum fixing pin 132, which is operated according to the manipulation in the handling unit 110 as described below. Therefore, it may be easily understood how the handling unit 110 and the external rotating drum 121 are fixed to each other.

Further, as shown in FIG. 14, the gyro link 115, particularly its gyro wheel, is connected to the roll sprocket 141 and thus may operate in the roll direction according to the rotation of the roll sprocket 141.

Figure 16:
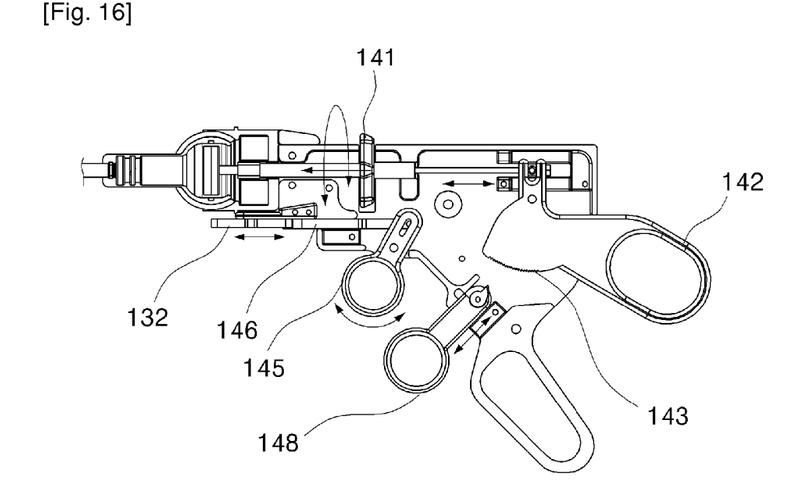
FIG. 16 shows the interior of the handling unit 110 according to one embodiment of the invention.

FIG. 16 shows the interior of the handling unit 110 according to one embodiment of the invention. In addition to the above-described rotating drum fixing pin 132 and roll sprocket 141, main elements of the handling unit 110 are shown in FIG. 16. Examples of the main elements may include an opening/closing handle 142 to control the opening/closing of the end effector 100; a latch gear 143 to convert the rotational motion of the opening/closing handle 142 to the forward and backward motion of opening/closing wires (and preferably to fix the opening/closing control state of the opening/closing handle 142); a fixing handle 145 to control the forward and backward motion (or the pin loosening/fastening motion) of the rotating drum fixing pin 132; and a sliding member 146 to convert the rotational motion of the fixing handle 145 to the forward and backward motion of the rotating drum fixing pin 132. There may be further provided an auxiliary handle 148 to restrict the rotational motion of the fixing handle 145 as necessary and firmly maintain the fixing of the handling unit and the external rotating drum as describe above.

When using the minimally invasive surgery instrument according to the above-described embodiments of the invention, the user may manipulate the handling unit 110 against the shaft 150 so that the end effector 100 carries out joint motion and is disposed at a surgery site; fix the handling unit 110 to the external rotating drum 121 to fix the above state of the joint motion; and rotate the roll sprocket 141 to roll the end effector 100. Therefore, the user may perform surgical actions (e.g., suturing by a round needle) on the surgical site delicately and conveniently.

Figure 17:
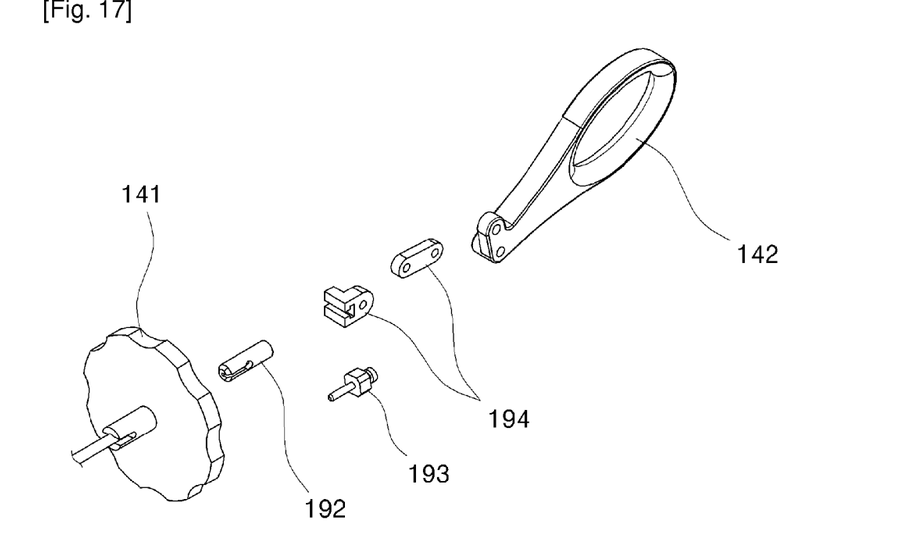
FIG. 17 is an exploded view showing the connection between a roll sprocket 141 and an opening/closing handle 142 according to one embodiment of the invention.
Figure 18:
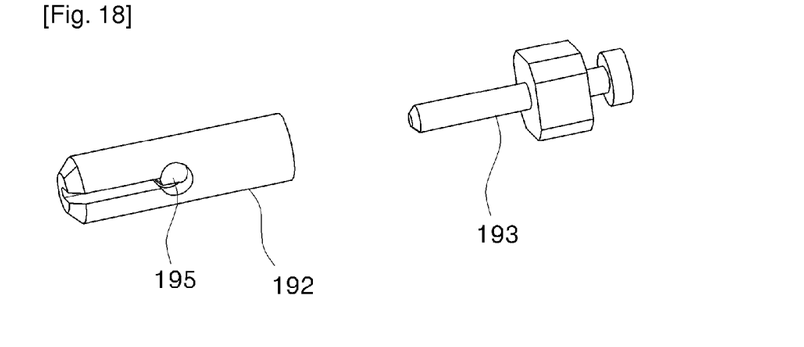
FIGS. 18 and 19 are enlarged perspective views of the above connection.
Figure 19:
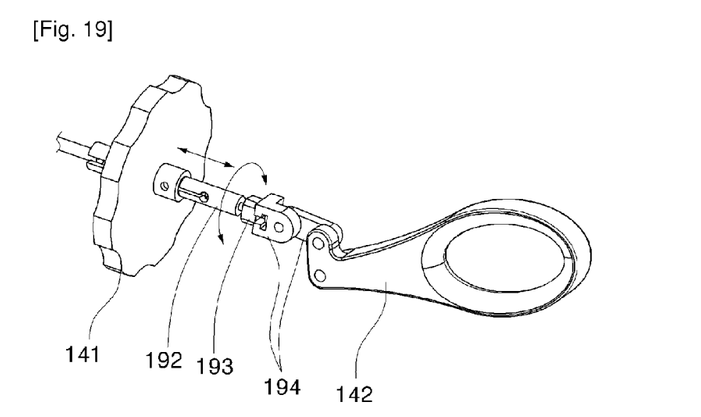

FIGS. 17-19 show the connection between the roll sprocket 141 and the opening/closing handle 142 according to one embodiment of the invention. FIG. 17 is an exploded view showing the connection between the roll sprocket 141 and the opening/closing handle 142 according to one embodiment of the invention. Further, FIGS. 18 and 19 are enlarged perspective views of the above connection.

As illustrated, the roll sprocket 141 and the opening/closing handle 142 may be connected via a ferrule insertion tube 192, a screw 193, a hinge 194 and the like. The ferrule insertion tube 192 is provided with a ferrule insertion hole 195 to which the ferrule of the opening/closing wire may be inserted and fixed. The screw 193 may be coupled to the ferrule insertion tube 192 in a manner of fastening/loosening the screw 193. In this case, the combined length of the ferrule insertion tube 192 and the screw 193 may vary as the number of fastening/loosening the screw 193. Thus, the user may adjust the combined length of the ferrule insertion tube 192 and the screw 193 before performing a surgery to set the tension of the opening/closing wire as necessary. Meanwhile, the hinge 194 may act together with or independently from the above-described latch gear 143 to convert the rotational motion of the opening/closing handle 142 to the forward and backward motion of the opening/closing wire.

Figure 20:
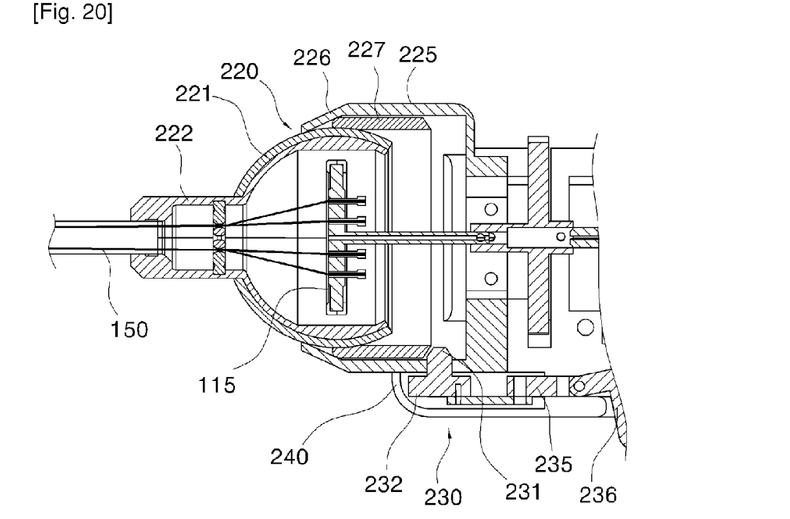
FIG. 20 shows the interior of a rotation manipulation unit 220 according to another embodiment of the invention.

FIG. 20 shows the interior of a rotation manipulation unit 220 according to another embodiment of the invention.

The configuration of the rotation manipulation unit 120 according to one embodiment of the invention has been discussed above with reference to FIG. 13 and the like. In the following, the configuration of the rotation manipulation unit 220 according to another embodiment of the invention will be discussed with reference to FIG. 20. The elements of the rotation manipulation unit 220 similar to those of the rotation manipulation unit 120 will not be described in detail.

The rotation manipulation unit 220 may comprise an external rotating drum 221; an internal rotating drum 222; a first rotating drum fixing member 225 to fix to the external rotating drum 221 by acting together with a second rotating drum fixing member 227 to be described below; the second rotating drum fixing member 227 to fix to the external rotating drum 221 by being inserted in a space between the external rotating drum 221 and the first rotating drum fixing member 225 and pressed by the first rotating drum fixing member 225; and a rotating drum fixing means 230 to insert the second rotating drum fixing member 227 in the space by moving forward the second rotating drum fixing member 227 from its default position.

More specifically, the front end 226 of the first rotating drum fixing member 225 may be fixed to or released from the external rotating drum 221. Thus, in each case, the handling unit 110 may be fixed to or released from the external rotating drum 221, and further fixed to or released from the shaft 150. To this end, the frond end 226 may be comprised of an elastic body spaced apart from the external rotating drum 221 at an interval from its default state.

Further, the second rotating drum fixing member 227 may be an annular member that may be pushed by a fixing screw 231 to carry out forward motion as the fixing screw 231 is fastened. When the second rotating drum fixing member 227 is not pushed by the fixing screw 231, it may carry out backward motion to return to its default position by the action of the first rotating drum fixing member 225, particularly by the action of the front end 226.

Meanwhile, the rotating drum fixing means 230 may comprise the fixing screw 231 having a shape to move forward the second rotating drum fixing member 227 as the fixing screw 231 is disposed at the handling unit 110 and fastened; and connecting members 235 and 236 being eccentrically connected to the head 232 of the fixing screw 231 to operate according to the rotational motion of the fixing handle (not shown), thereby rotating the fixing screw 231.

Figure 21:
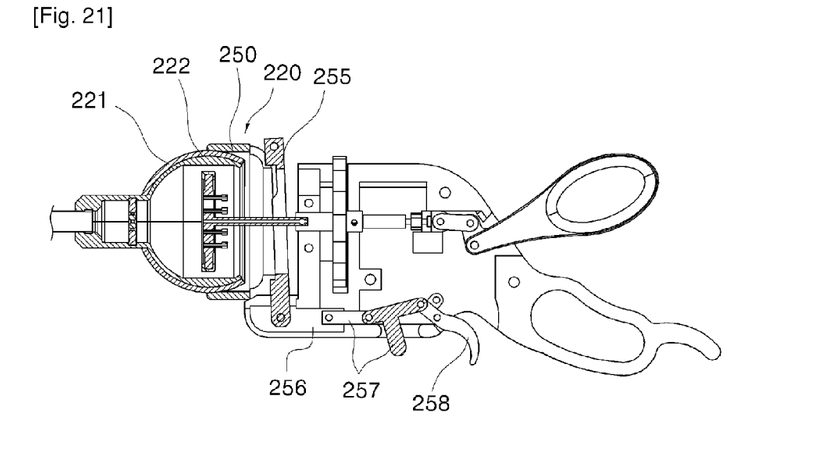
FIG. 21 is a diagram of a rotation manipulation unit 220 according to yet another embodiment of the invention.

FIG. 21 is a diagram of a rotation manipulation unit 220 according to yet another embodiment of the invention. The rotation manipulation unit 220 shown in FIG. 21 is configured to achieve the fixing to the external rotating drum 221 in a manner different from that of the rotation manipulation unit 220 shown in FIG. 20.

The rotation manipulation unit 220 may comprise an external rotating drum 221; an internal rotating drum 222; a pressure drum 250 surrounding the external rotating drum 221 to apply pressure to the external rotating drum 221 to achieve the fixing thereto; a pushing plate 225 to push the pressure drum 250 to the external rotating drum 221; and connecting members 256, 257 and 258 being connected to the lower end of the pushing plate 255 to rotate and push the pushing plate 255 according to some manipulation.

According to the above configuration, the connecting members 256, 257 and 258 may be manipulated to sequentially act to move the lower end of the pushing plate 255 in the direction opposite to the end effector 100 and the upper end of the pushing plate 255 in the direction of the end effector 100. When the upper end of the pushing plate 255 pushes the pressure drum 250 in the direction of the end effector 100, the pressure drum 250 surrounding the external rotating drum 221 may apply pressure to the external rotating drum 221 to achieve the fixing thereto.

Meanwhile, when the pushing plate 255 moves contrary to the above, the pressure applied to the external rotating drum 221 by the pressure drum 250 is released so that the fixing to the external rotating drum 221 may also be eventually released.

According to an application of the present invention, at least a part of the handling unit 110 of the minimally invasive surgical instrument may be changed or modified to some components suitable to be driven by a motor-based system (not shown) such as a surgical robot, so that the minimally invasive surgical instrument may be configured to be controlled by an automatic (or semi-automatic) manipulation system rather than the user's manual manipulation.

For example, an electric motor (not shown) included in a surgical robot may enable the end effector 100 to carry out joint motion by directly operating the gyro wheel of the gyro link 115 in the pitch or yaw direction. For another example, the electric motor may enable the end effector 100 to carry out joint motion in the joint unit 160 by directly operating a wheel in the rotation manipulation unit 120 in the pitch or yaw direction. For yet another example, the electric motor may enable the end effector 100 to carry out joint motion in the joint unit 160 by directly pulling some of the plurality of wires P-W1, Y-W1, P-W2 and Y-W2. Obviously, the electric motor may enable the end effector 100 to carry out joint motion by directly manipulating the modified handling unit 110.

For another example, the electric motor may enable the end effector 100 to roll by directly rotating the gyro wheel of the gyro link 115 or the roll sprocket 141.

For yet another example, the electric motor may control the opening or closing of the pincers 101 by directly pulling the opening/closing wires.

For still another example, a system may fix the joint motion state, rolling state, or opening/closing state of the end effector 100 by directly controlling the drive of the electric motor.

Although the present invention has been described in terms of specific items such as detailed elements as well as the limited embodiments and the drawings, they are only provided to help general understanding of the invention, and the present invention is not limited to the above embodiments. It will be appreciated by a person of ordinary skill in the art that various modifications and changes may be made from the above description.

Therefore, the spirit of the present invention shall not be limited to the above-described embodiments, and the entire scope of the appended claims and their equivalents will fall within the scope and spirit of the invention.

What is claimed is:

1. A minimally invasive surgical instrument comprising:
   a shaft;
   an end effector being connected to one end of the shaft via a joint unit;
   a rotation manipulation unit being connected to the other end of the shaft, the rotation manipulation unit comprising a gyro link including a gyro wheel, an external rotating drum, and an internal rotating drum, wherein the pitch and the yaw direction operations of the internal rotating drum are restricted by the external rotating drum and at least a part of the internal rotating drum is disposed in the external rotating drum,
   wherein the gyro link is disposed in and connected to the internal rotating drum to operate in a roll direction together with the internal rotating drum and the gyro wheel operates in the roll direction when the external rotating drum is fixed; and
   a plurality of wires being connected between the joint unit and the gyro wheel, wherein the end effector carries out joint motion by the joint unit according to the action of at least some of the plurality of wires caused by a manipulation of the gyro wheel.

2. A minimally invasive surgical instrument as claimed in claim 1, wherein the joint unit comprises:
   a plurality of joint links; and
   joints for pitch direction operation and joints for yaw direction operation being formed with at least one of the plurality of joint links being interposed therebetween.

3. A minimally invasive surgical instrument as claimed in claim 2, wherein in the joint unit, there are provided at least two joints for pitch direction operation and at least two joints for yaw direction operation, and the at least two joints for pitch direction operation and the at least two joints for yaw direction operation are alternately disposed.

4. A minimally invasive surgical instrument as claimed in claim 2, wherein at least one of the plurality of joint links comprises a rotating link member at one end and another rotating link member at the other end, and the another rotating link member is disposed in the direction substantially perpendicular to the direction in which the rotating link member is disposed.

5. A minimally invasive surgical instrument as claimed in claim 2, wherein at least one of the plurality of joint links has a slope for the joint motion.

6. A minimally invasive surgical instrument as claimed in claim 2, wherein the joint unit further comprises a connecting unit for connection with the end effector;
the plurality of joint links and the connecting unit comprise via holes, respectively; and
each of the plurality of wires is hung in one of the plurality of joint links and the connecting unit via the corresponding via hole.

7. A minimally invasive surgical instrument as claimed in claim 1, wherein the gyro wheel comprises an inner via hole and an outer via hole.

8. A minimally invasive surgical instrument as claimed in claim 7, wherein each of the plurality of wires hangs in one of the inner via hole and the outer via hole.

9. A minimally invasive surgical instrument as claimed in claim 8, wherein the wires hung in the outer via hole among the plurality of wires are intended for the joints closer to the end effector than the shaft among a plurality of joints in the joint unit.

10. A minimally invasive surgical instrument as claimed in claim 1, wherein at least some of the plurality of wires are pushed or pulled as the gyro wheel operates in a pitch or yaw direction.

11. A minimally invasive surgical instrument as claimed in claim 10, wherein the rotation manipulation unit further comprises a fixing means to fix the state of the operation of the gyro wheel.

12. A minimally invasive surgical instrument as claimed in claim 11, wherein the gyro wheel may operate in the roll direction while the operation of the gyro wheel is restricted.

13. A minimally invasive surgical instrument as claimed in claim 1, wherein the gyro wheel may operate in a roll direction.

14. A minimally invasive surgical instrument as claimed in claim 1, wherein the external rotating drum may be fixed by an annular rotating drum fixing member and the internal diameter of the rotating drum fixing member may be reduced.

15. A minimally invasive surgical instrument as claimed in claim 1, wherein the rotation manipulation unit further comprises:
a first rotating drum fixing member being spaced apart from the external rotating drum at an interval and surrounding at least a part of the external rotating drum; and
a second rotating drum fixing member being inserted in a space between the external rotating drum and the first rotating drum fixing member to fix the external rotating drum.

16. A minimally invasive surgical instrument as claimed in claim 15, wherein the second rotating drum fixing member is inserted in the space as a fixing screw is fastened.

17. A minimally invasive surgical instrument as claimed in claim 1, wherein the external rotating drum may be fixed by a pressure drum.

18. A minimally invasive surgical instrument as claimed in claim 1, further comprising a handling unit being connected to the rotation manipulation unit to operate in a pitch or yaw direction together with the gyro wheel.

19. A minimally invasive surgical instrument as claimed in claim 18, wherein the operation of the handling unit may be restricted in relation to the shaft.

20. A minimally invasive surgical instrument as claimed in claim 18, wherein the handling unit further comprises a roll sprocket to operate the gyro wheel in a roll direction.

21. A minimally invasive surgical instrument as claimed in claim 1, further comprising an electric driving motor to operate the gyro wheel in a pitch or yaw direction.

22. A minimally invasive surgical instrument as claimed in claim 1, further comprising an electric driving motor to operate the gyro wheel in a roll direction.

* * * * *